(12) United States Patent
Liscio (10) Patent No.: US 12,214,179 B2
(45) Date of Patent: Feb. 4, 2025

(54) INJECTOR DEVICE

(71) Applicant: SANOFI, Paris (FR)

(72) Inventor: Edward Liscio, Bridgewater, NJ (US)

(73) Assignee: SANOFI, Paris (FR)

( * ) Notice: Subject to any disclaimer, the term of this patent is extended or adjusted under 35 U.S.C. 154(b) by 306 days.

(21) Appl. No.: 17/956,420

(22) Filed: Sep. 29, 2022

(65) Prior Publication Data

US 2023/0038424 A1    Feb. 9, 2023

Related U.S. Application Data

(63) Continuation of application No. 16/753,838, filed as application No. PCT/EP2018/079688 on Oct. 30, 2018, now Pat. No. 11,464,917.

(30) Foreign Application Priority Data

Oct. 30, 2017   (EP) ..................................... 17306489

(51) Int. Cl.
*A61M 5/32* (2006.01)
*A61M 5/20* (2006.01)
(Continued)

(52) U.S. Cl.
CPC ........ *A61M 5/3245* (2013.01); *A61M 5/2033* (2013.01); *A61M 5/31513* (2013.01);
(Continued)

(58) Field of Classification Search
CPC ........ A61M 5/2466; A61M 2005/2474; A61M 5/3257; A61M 2005/3258; A61M 5/326;
(Continued)

(56) References Cited

U.S. PATENT DOCUMENTS

2011/0257603 A1  10/2011  Ruan et al.
2013/0197474 A1   8/2013  Bilton et al.
(Continued)

FOREIGN PATENT DOCUMENTS

CN    102821802    12/2012
CN    105764548     7/2016
(Continued)

OTHER PUBLICATIONS

International Preliminary Report on Patentability in Application No. PCT/EP2018/079688, dated May 5, 2020, 10 pages.
(Continued)

*Primary Examiner* — Nilay J Shah
(74) *Attorney, Agent, or Firm* — Bond, Schoeneck & King, PLLC (57) ABSTRACT

An injector device includes a housing for receiving a medicament cartridge; a needle unit comprising a needle; and a first sleeve slideable along a longitudinal axis of the housing from a first position, in which the first sleeve conceals the needle, to a second position, in which the needle is exposed from an end of the first sleeve, the first sleeve configured to engage the needle unit so that, during use, movement of the first sleeve from the first position to the second position moves the needle unit from a primary position to a secondary position, in which secondary position the needle unit locates over an end of a medicament cartridge, wherein the device further comprises a second sleeve arranged to move telescopically with respect to the first sleeve, the first sleeve extending from the second sleeve when the first sleeve is in the first position.

18 Claims, 6 Drawing Sheets

(51) Int. Cl.
*A61M 5/315* (2006.01)
*A61M 5/24* (2006.01)

(52) U.S. Cl.
CPC ..... *A61M 5/3257* (2013.01); *A61M 2005/206* (2013.01); *A61M 2005/208* (2013.01); *A61M 5/2466* (2013.01); *A61M 2005/3247* (2013.01); *A61M 2005/3267* (2013.01)

(58) Field of Classification Search
CPC ........ A61M 2005/3267; A61M 5/3243; A61M 5/3245; A61M 5/2033; A61M 2005/208; A61M 2005/206; A61M 2005/2073
See application file for complete search history.

(56) References Cited

U.S. PATENT DOCUMENTS

| | | |
|---|---|---|
| 2015/0126925 A1 | 5/2015 | Fuke et al. |
| 2016/0279339 A1 | 9/2016 | Schenker et al. |
| 2016/0287787 A1 | 10/2016 | Riedel |
| 2017/0304542 A1 | 10/2017 | Helmer |

FOREIGN PATENT DOCUMENTS

| | | | |
|---|---|---|---|
| CN | 106456892 | 2/2017 | |
| JP | 2017-522928 | 8/2017 | |
| WO | WO 2011/095488 | 8/2011 | |
| WO | WO 2014/016889 | 1/2014 | |
| WO | WO 2015/150578 | 10/2015 | |
| WO | WO 2015/185664 | 12/2015 | |
| WO | WO-2015185664 A1 * | 12/2015 | .......... A61M 5/2466 |
| WO | WO 2017/089276 | 6/2017 | |
| WO | WO 2017/114934 | 7/2017 | |

OTHER PUBLICATIONS

International Search Report and Written Opinion in Application No. PCT/EP2018/079688, dated Dec. 13, 2018, 12 pages.

* cited by examiner

SECTION A-A
FIG. 5A

FIG. 5B

INJECTOR DEVICE

CROSS-REFERENCE TO RELATED APPLICATIONS

The present application is a continuation of U.S. patent application Ser. No. 16/753,838, filed on Apr. 6, 2020, which is the national stage entry of International Patent Application No. PCT/EP2018/079688, filed on Oct. 30, 2018, and claims priority to Application No. EP 17306489.0, filed on Oct. 30, 2017, the disclosures of which are incorporated herein by reference.

TECHNICAL FIELD

The present disclosure relates to an injector device for a medicament.

BACKGROUND

Cartridge injection devices, for example cartridge auto-injectors, typically have a sealed cartridge that contains a medicament, and a needle that is initially separated from the cartridge. An initial action moves the cartridge and needle together so that the needle pierces the cartridge. A plunger can then be moved into the cartridge to dispense medicament through the needle for injection to a user.

SUMMARY

In certain aspects, an advantageous injector device is provided. The injector device has a housing for receiving a medicament cartridge; a needle unit comprising a needle; and a first sleeve slideable along a longitudinal axis of the housing from a first position, in which the first sleeve conceals the needle, to a second position, in which the needle is exposed from an end of the first sleeve, the first sleeve configured to engage the needle unit so that, during use, movement of the first sleeve from the first position to the second position moves the needle unit from a primary position to a secondary position, in which secondary position the needle unit locates over an end of the medicament cartridge when the medicament cartridge is received in the device, wherein the device further comprises a second sleeve arranged to move telescopically with respect to the first sleeve, the first sleeve extending from the second sleeve when the first sleeve is in the first position.

Therefore, prior to use of the device, the needle unit and needle are spaced from the cartridge. This has the advantage that the cartridge remains sealed up until the time that the device is required for use.

As the first sleeve is moved from the first position to the second position the first sleeve may disengage from the needle unit thereby allowing the first sleeve to move independently of the needle unit.

The first sleeve and the second sleeve may be arranged such that, during use, when the first sleeve is displaced along the longitudinal axis and when an end of the first sleeve is flush with an end of the second sleeve, the needle unit engages the cartridge.

Advantageously, this configuration provides a two-step injection initiation process which is discernible to the user.

Throughout the range of movement of the first sleeve from the first position to the position in which the needle unit engages the cartridge, the needle may be concealed.

Therefore the needle is not exposed prior to the device being in a state ready for use, that is to say, prior to the needle unit having moved onto the cartridge.

Throughout the range of movement of the first sleeve from the position in which the needle unit engages the cartridge to the second position, the second sleeve may move simultaneously with the first sleeve to expose the needle.

A spring may be provided to resist movement of the second sleeve.

Advantageously, a degree of resistance to movement of the second sleeve helps, to some degree, to control the speed with which the needle penetrates tissue which increases the comfort of the user.

The device may further comprise a plunger displaceable to drive medicament from the cartridge and a plunger mechanism triggerable to displace the plunger during operation of the device.

Therefore the plunger can be mechanically, rather than manually, operated to ensure consistent delivery characteristics.

Either the first sleeve or the second sleeve may be configured to trigger the plunger during displacement along the longitudinal axis.

Therefore medicament is automatically delivered during injection.

The first sleeve may comprise a resiliently displaceable arm extending into the housing and into contact with the needle unit, wherein the resiliently displaceable arm is configured to disengage the needle unit by moving away from the longitudinal axis as the first sleeve is moved from the first position to the second position, thereby allowing the first sleeve to move independently of the needle unit.

The needle unit may comprise a protrusion, the displaceable arm comprising a corresponding opening through which the protrusion is locatable to connect said arm to said needle unit.

The protrusion may be shaped so that, during use, with the needle unit located against the cartridge, further axial movement of the first sleeve causes the protrusion to displace the arm away from the longitudinal axis, and out of engagement with the needle unit.

Therefore, the protrusion and the opening are easily disengageable to allow the sleeve to move independently of the needle unit.

The arm may comprise an elongate slot distal to the opening to provide a track for the protrusion during said further axial movement of the arm.

Therefore the arm may continue to be displaced into the housing following disengagement of with the needle unit, unencumbered by the protrusion.

An end of the displaceable arm may be further provided with a clip, the clip being configured to lock over an edge of the cartridge when the first sleeve is in the second position.

The sleeve may be provided with a ledge, the ledge being configured to abut the needle unit when the sleeve is in the second position, so that the needle unit is held over the end of the cartridge by the ledge.

Therefore, the sleeve is secured in the second position by the clip and the needle unit is prevented from moving by the ledge. This has the advantage that the needle unit and the cartridge remain combined throughout the injection procedure.

The arm may be provided with a delimitation to allow a portion of the arm comprising the elongate slot and the opening to move independently of the clip.

Therefore the portion of the arm comprising the clip may be displaced without the arm disengaging the needle unit.

The device may further comprise a medicament cartridge.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

Figure 1A:
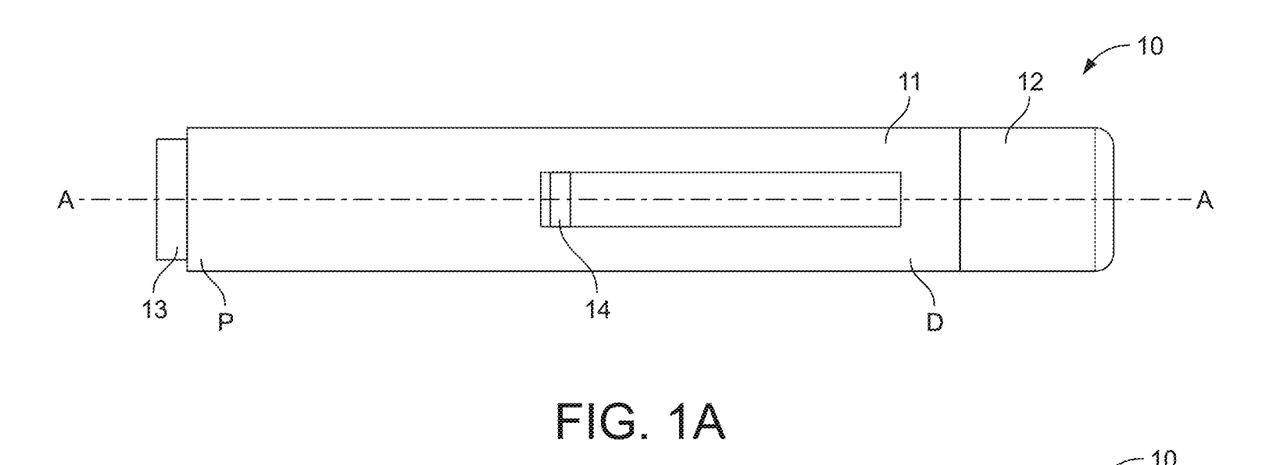
FIG. 1A is a schematic side view of an injector device, and a removable cap.
Figure 1B:
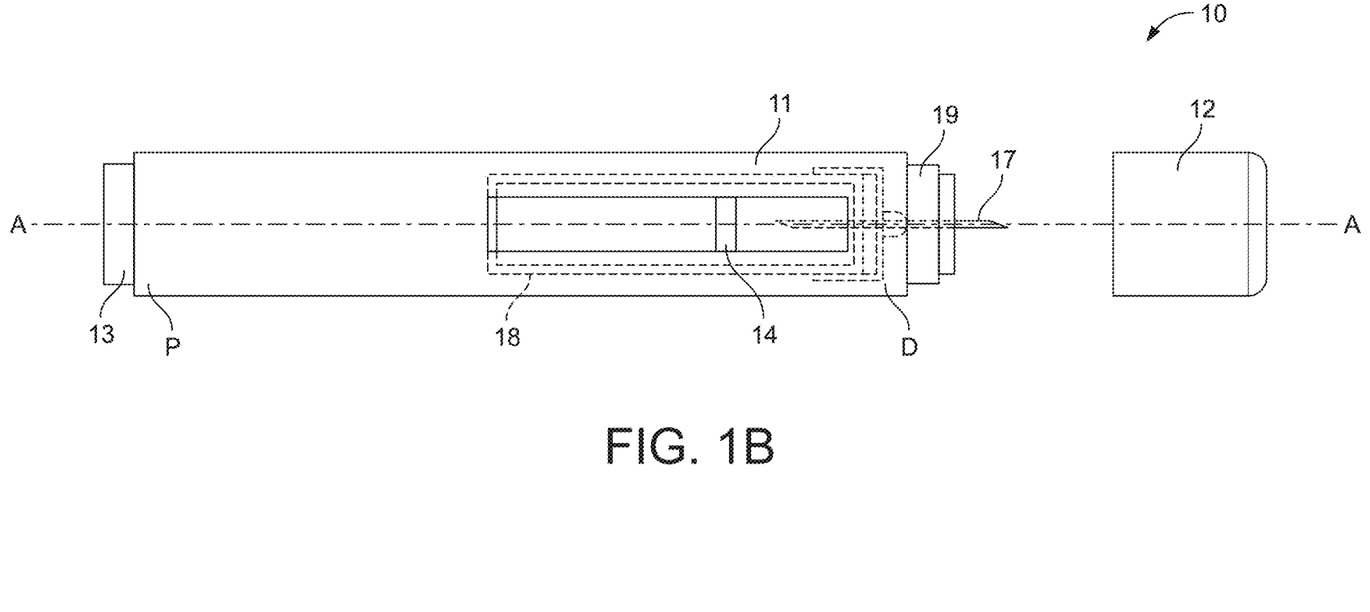
FIG. 1B is a schematic side view of the injector device of FIG. 1A, with the cap removed from the housing.

The one or more automated functions of an auto-injector may each be activated via an activation mechanism. Such an activation mechanism can include an actuator, for example, one or more of a button 13 (as shown in FIGS. 1A and 1B), a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Figure 2:
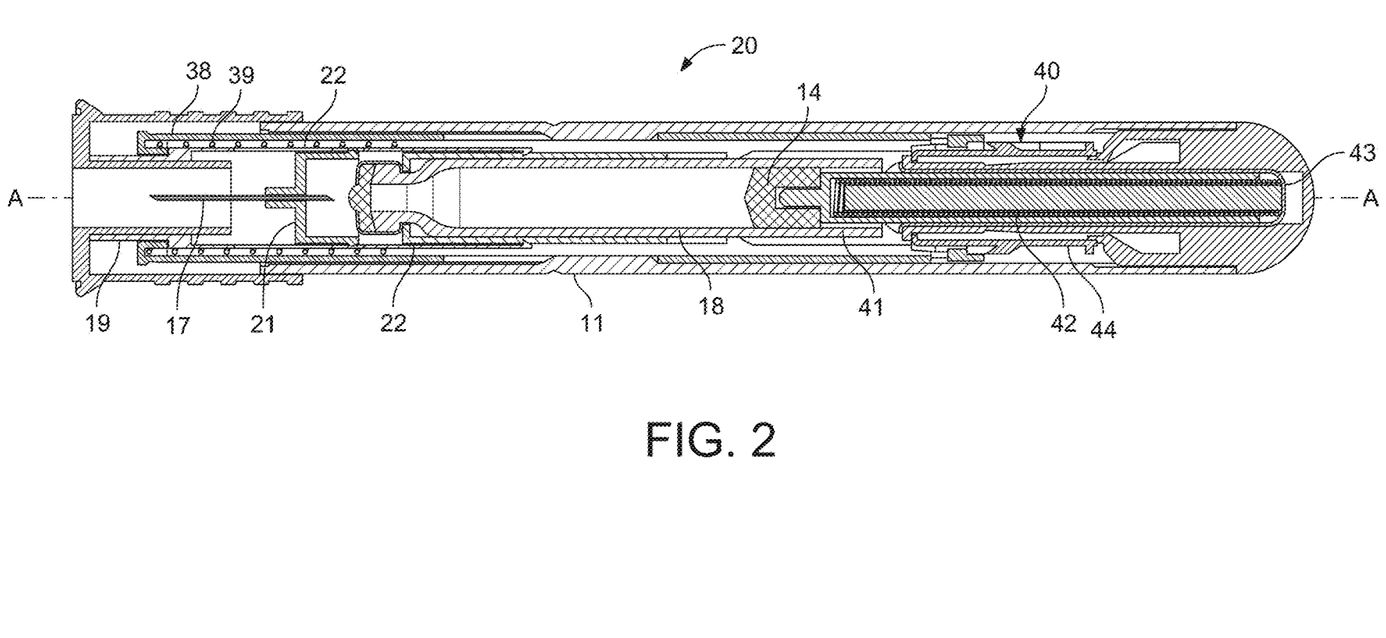
FIG. 2 shows an injector device.

FIG. 2 shows a second injector device 20, wherein like features retain the same reference numbers, comprising: a housing 11; a medicament cartridge 18 disposed within the housing 11 in a medicament cartridge holder 45; a needle unit 21 comprising a needle 17; a sleeve 19 slideable along a longitudinal axis A-A of the housing 11 from a first position, in which the sleeve 19 conceals the needle 17, to a second position, in which the needle 17 is exposed from an end of the sleeve 19.

The device comprises a cap 12 which must be removed prior to use. The cap 12 attaches over the distal end of the housing 11 to enclose the end of the sleeve 19. Prior to an injection event the cap 12 is removed then, to begin injection, the user places the end of the sleeve 19 across an injection site and presses the device 20 downwards to displace the sleeve 19 from the first position into the second position.

Prior to use of the device 20, the needle unit 21 is in a primary position in which the needle 17 and needle unit 21 are spaced from the cartridge 18. During use, the needle unit 21 is moved over the end of the cartridge 18 into a secondary position to fluidly connect the needle 17 with the cartridge 18. This has the advantage that the cartridge 18 remains sealed up until the time that the device 20 is required for use.

To achieve this the sleeve 19 extends into the housing 11 and into contact with the needle unit 21 so that, during use, movement of the sleeve 19 from the first position to the second position simultaneously moves the needle unit 21 over the end of the cartridge 18. In the illustrated example the sleeve is provided with a resiliently displaceable arm 22 that extends into contact with the needle unit 21.

In the illustrated example, the two displaceable arms 22 are shown that extend into contact with opposite sides of the needle unit 21. However, it shall be appreciated that any number of arms may serve to achieve the same effect, including a single arm 22.

Each resiliently displaceable arm 22 of the illustrated example is configured to disengage the needle unit 21 by moving away from the longitudinal axis A-A of the device 20 as the sleeve 19 is moved from the first position to the second position, allowing the sleeve 19 to move independently of the needle unit 21. Therefore, during use, once the needle unit 21 has moved onto the cartridge 18, the sleeve 19 may then continue to be displaced into the second position to expose the needle 17 so that it enters the injection site, as explained above.

Figure 3A:
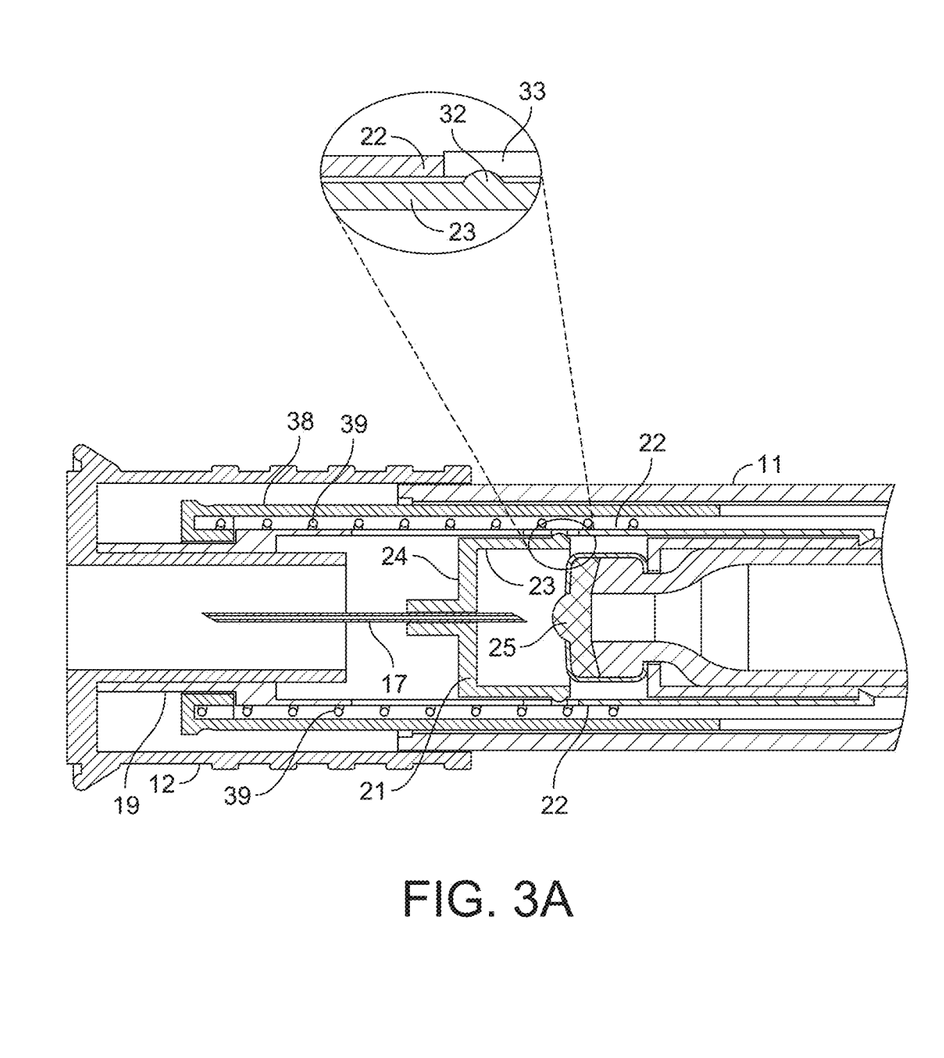
FIG. 3A is a detail view of the injector device.
Figure 3B:
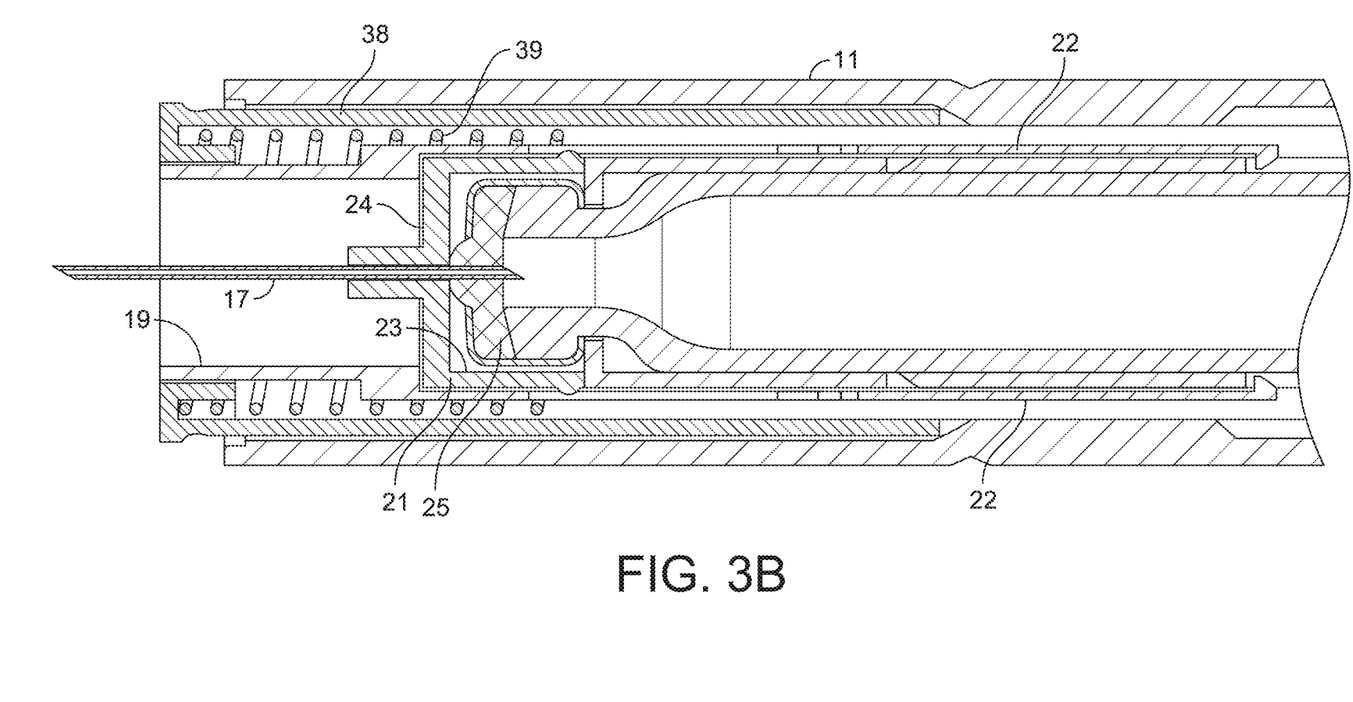
FIG. 3B is a detail view of the injector device.

With reference to FIGS. 3A and 3B, the needle unit 21 and cartridge 18 connect as follows. The needle unit 21 comprises a circumferential wall 23 and an end wall 24, the end wall 24 closing an edge of the circumferential wall 23 to form a cap shape. The space enclosed by the circumferential and end walls 23, 24 is herein referred to as a cartridge receiving space.

The needle 17 extends centrally through the end wall 24 of the needle unit 21 and is rigidly secured about a midpoint, so that a first portion of the needle extends toward a proximal end of the device and a second portion of the needle extends into the cartridge receiving space of the needle unit 21. The second portion of the needle 17 penetrates a seal 25 in the distal end of the cartridge 18 as the needle unit 21 and cartridge 18 are combined, as shown in FIG. 3B. The seal 25 may be a rubber bung or foil cover, for example. When the needle unit 21 is in the secondary position the end wall 24 abuts an edge of the cartridge holder 45 to prevent further axial movement of the needle unit 21 toward the proximal end of the device 20.

Figure 4A:
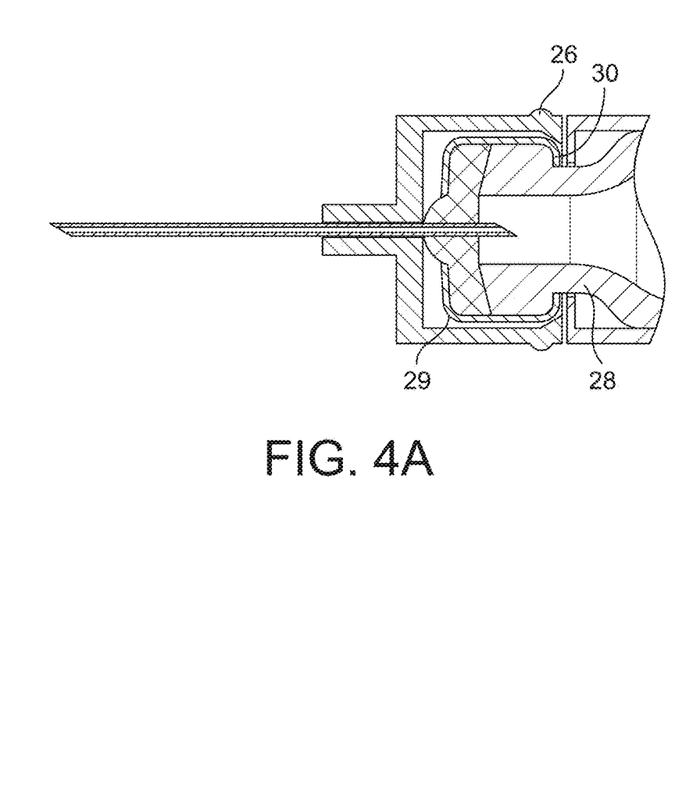
FIG. 4A is a detail view of the injector device.
Figure 4B:
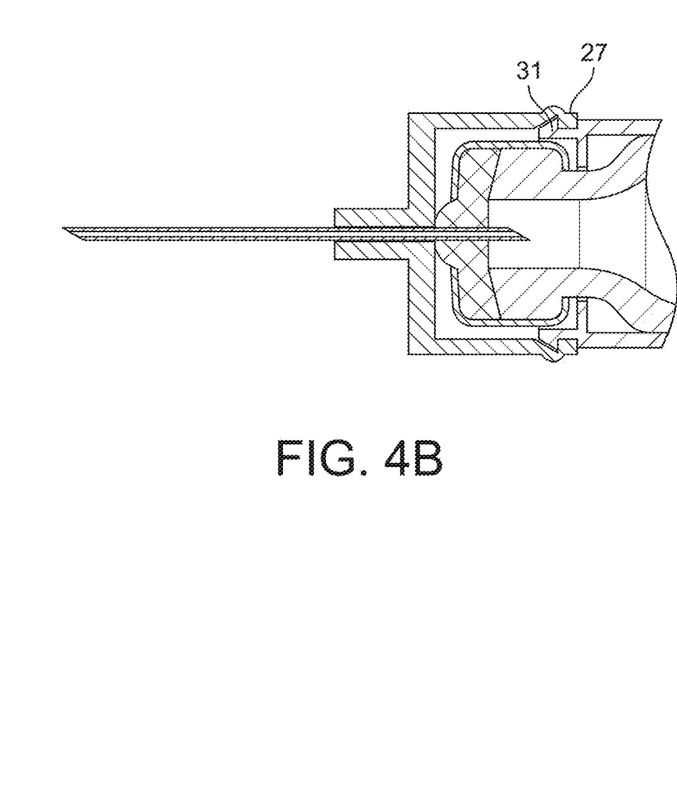
FIG. 4B is a detail view of the injector device.

The needle unit 21 may be provided with a clip 26, 27 to lock the needle unit 21 onto the end of the cartridge 18 as shown in FIGS. 4A and 4B. In a first example shown in FIG. 4A the distal end of the cartridge 18 comprises a neck portion 28 and a head portion 29. The neck portion 28 is a narrower portion of the cartridge 18 into which the clip 26 of the needle unit 21 may locate. The head portion 29, being wider than the neck portion 28, provides a rim 30 which abuts the clip 26 to prevent movement of the needle unit 21 toward the distal end of the device 20 once the needle unit 21 and the cartridge 18 are combined. In a second example shown in FIG. 4B, the clip 27 cooperates with a corresponding clip 31 on an internal wall of the device. The clip on the needle unit 21 and internal wall of the device may be barbed and resiliently displaceable. Thus, the clips 27, 31 may deflect to pass over each other and engage in a locked state to prevent the needle unit 21 moving toward the distal end of the device 20 once the needle unit 21 and the cartridge 18 are combined.

As best illustrated by FIG. 3A, the circumferential wall 23 of the needle unit 21 comprises a protrusion 32 which is configured to engage a corresponding opening 33 in the displaceable arm 22 of the sleeve 19. The protrusion 32 is locatable in said opening 33 to connect the displaceable arm 22 to the needle unit 21. In use, the displaceable arm 22 and the needle unit 21 remain connected in this way until the needle unit 21 has moved onto the distal end of the cartridge 18. Thereafter, further movement of the sleeve 19 between the first and second positions disengages the arm 22 from the needle unit 21.

The protrusion 32 is shaped to facilitate the disengagement of the arm 22 and the needle unit 21. For example the protrusion 32 may be rounded. In use, when the needle unit 21 is located over the end of the cartridge 18, the cartridge 18 and the end wall 24 of the needle unit 21 abut, preventing further movement of the needle unit 21 toward the proximal end of the device. With the needle unit 21 so located, the user will continue to press the device 20 toward the injection site, moving the sleeve 19 into the second position. This further movement of the sleeve 19 causes the displaceable arms 22 to be pushed outward over the rounded shape of the protrusion 32 to disengage the protrusion 32 and the opening 33.

Figure 5A:
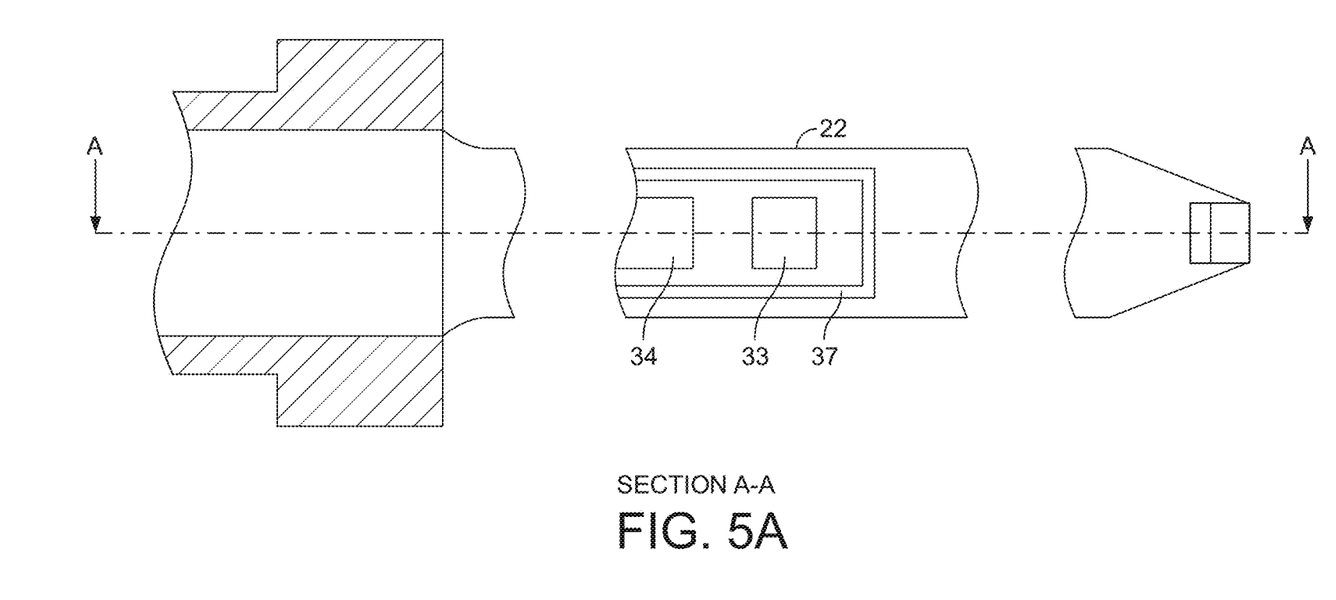
FIG. 5A is a detail view of the injector device.
Figure 5B:
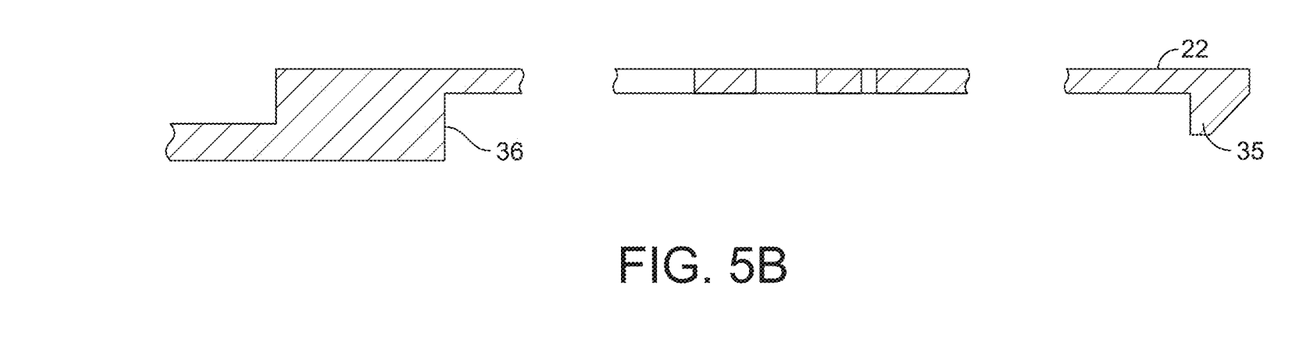
FIG. 5B is a detail view of the injector device.

As best illustrated by FIGS. 5A and 5B, the displaceable arm 22 may comprise an elongate slot 34 distal to the opening 33 to provide a track for the protrusion 32. When, in use, the displaceable arm 22 and the needle unit 21 have disengaged the slot 34 allows the displaceable arm 22 to spring back toward the longitudinal axis A-A by accommodating the protrusion 32. This serves the advantage that the displaceable arm 22 can move toward the proximal end of the device 20 and into the second position without interference from the protrusion 32.

An end of the displaceable arm 22 may further be provided with a clip 35, the clip 35 being configured to lock over an edge of the cartridge 18 when the sleeve is in the second position. The clip 35 acts to retain the sleeve 19 in the second position. Further, the sleeve 19 may be provided with a ledge 36 which depends from an internal surface of the sleeve 19, that is to say a surface of the sleeve 19 facing the longitudinal axis A-A. The ledge 36 is configured to abut the end wall 24 of the needle unit 21 to hold the needle unit 21 on the cartridge 18 when the sleeve 19 is in the second position.

In another example, the displaceable arm 22 is also provided with a delimitation 37 as shown in FIG. 5A. The delimitation 37 allows a portion of the arm 22 enclosed by the delimitation 37 to move independently of the clip 35. Said portion of the arm 22 comprises the elongate slot 32 and the opening 33. Therefore the clip 35 can be displaced outward as the sleeve 19 is moved between the first and second positions without disengaging the opening 33 in the arm 22 from the protrusion 32 on the needle unit 21. The delimitation can be for example but not limited to a cut out portion.

In the illustrated examples, the device 20 further comprises a second sleeve 38 arranged to move telescopically with respect to the above mentioned sleeve 19, herein referred to as the first sleeve 19. In this example the first sleeve 19 slides within the second sleeve 38, the first sleeve 19 extending from the second sleeve 38 when the first sleeve 19 is in the first position. During use, the first sleeve 19 is displaced along the longitudinal axis A-A as the user pushes the device 20 toward the injection site. At a point of displacement between the first and second positions, the end of the first sleeve 19 is flush with the end of the second sleeve 38, thereafter the first and second sleeves 19, 38 are simultaneously displaced into the housing 11 until the first sleeve 19 is in the second position.

Advantageously, this configuration provides a two step injection initiation process which is discernible to the user. Specifically, in a first step, the device 20 is pressed toward the injection site so that the first sleeve 19 is displaced toward the proximal end of the device 20 until the ends of the first and second sleeves 19, 38 are flush. The first and second sleeves 19,38 may be arranged, such that, completion of the first step signifies that the needle unit 21 and the cartridge 18 have been combined. That is to say, when the ends of the first and second sleeves 19, 38 are flush, the needle 17 has been fluidly connected to the cartridge 18. In a second step, the user continues to press the device 20 toward the injection site to cause simultaneous displacement of the first and second sleeves 19, 38, exposure of the needle 17 and needle penetration of the injection site.

Another advantage of this arrangement is that throughout the range of movement of the first sleeve 19 from the first position to the position in which the needle unit 21 engages the cartridge 18, the needle 17 may be concealed. This prevents the needle 17 penetrating the injection site prior to the needle 17 being fluidly engaged with cartridge 18.

A spring 39 is provided to resist movement of the second sleeve 38. It shall be appreciated that throughout movement of the second sleeve 38 the needle is extends from the device 20 into the injection site. A degree of resistance to movement of the second sleeve 38 helps, to some degree, to control the speed with which the needle 17 penetrates tissue which increases the comfort of the user.

As shown in FIG. 2, the device 20 may further comprise a plunger 14 displaceable to drive medicament from the cartridge and a plunger mechanism 40 triggerable to the displace the plunger 14 during operation of the device 20. The plunger mechanism 40 is disposed in the housing 11 at a proximal end of the device 20 and comprises a shaft 41 which is mechanically coupled to the plunger 14. The shaft 41 is further coupled to a biasing member 42, in this case a coil spring 42 which, when the plunger mechanism 40 is triggered, is displaced along the longitudinal axis A-A of the device 20 to displace the plunger 14 and drive medicament from the cartridge 18.

In the illustrated example, the shaft 41 is hollow having a closed distal end which is coupled to the plunger 14. The spring 42 is disposed in the hollow part of the shaft 41 with one end of the spring 42 abutting the closed end of the shaft 41 and the other end of the spring 42 abutting a reaction surface 43. The reaction surface 43 is fixed relative to the housing 11, so that, when the plunger mechanism 40 is triggered, extension of the spring 42 between the reaction surface 43 and the closed end of the shaft 41 displaces the shaft 41 away from the reaction surface 43 and pushing the plunger 14 into the cartridge 18.

The illustrated plunger mechanism 40 further comprises a collar 44, the collar 44 being rotatable about the longitudinal axis A-A between a locked position, in which the spring 42 is locked in place, and an unlocked position, in which the spring 42 is free to displace the plunger 14.

The collar cooperates with locking arms (not shown) that hold the shaft 41 against the force of the spring 42, prior to operation of the device 20.

The arms are inherently biased away from the shaft 41, however, with the collar 44 in the locked position, the collar 44 holds the arms against the shaft 41. Rotation of the collar 44 into the unlocked position releases the locking arms so that they spring outwards to release the shaft 41.

Either the first sleeve 19 or the second sleeve 38 may be configured to trigger the plunger mechanism 40 during displacement along the longitudinal axis A-A. For example, a follower surface of the collar 44 (not shown) may abut a distal edge (not shown) of either sleeve 19, 38, which distal edge is inclined relative to a direction perpendicular to the longitudinal axis A-A, so that, during axial displacement of the respective sleeve 19, 38, the collar 44 is rotated by said inclined edge about the axis A-A from the locked position into the unlocked position.

Alternatively, the collar 44 may comprise a protrusion (not shown) which engages a track (not shown) in the respective sleeve 19, 38. The track may be curved so that movement of the sleeve 19, 38 relative to the collar 44 causes the protrusion to follow the curved path of the track and therefore rotate the collar 44.

It can be envisaged that the sleeve is a first sleeve or a second sleeve.

The injector device may further comprise a reservoir of medicament in the medicament cartridge.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injector device comprising:
   a housing for receiving a medicament cartridge;
   a needle unit comprising a needle;
   a first sleeve slidable along a longitudinal axis of the housing from a first position, in which the first sleeve conceals the needle, to a second position, in which the needle is exposed from an end of the first sleeve,
      wherein the first sleeve is configured to engage the needle unit so that, during use, movement of the first sleeve from the first position to the second position moves the needle unit from a primary position to a secondary position, and
      wherein, in the secondary position, the needle unit is located over an end of the medicament cartridge when the medicament cartridge is received in the injector device; and
   a second sleeve arranged to move telescopically with respect to the first sleeve, the first sleeve configured to extend from the second sleeve when the first sleeve is in the first position, wherein the first sleeve comprises a resiliently displaceable arm extending into the housing and into contact with the needle unit, wherein the resiliently displaceable arm is configured to disengage from the needle unit by moving away from the longitudinal axis as the first sleeve is moved from the first position to the second position, thereby allowing the first sleeve to move independently of the needle unit.

2. The injector device according to claim 1, wherein the first sleeve and the second sleeve are arranged such that, during use, when the first sleeve is displaced along the longitudinal axis and when the end of the first sleeve is flush with an end of the second sleeve, the needle unit engages the cartridge.

3. The injector device according to claim 2, wherein throughout a range of movement of the first sleeve from the first position to a position in which the needle unit engages the cartridge, the needle is concealed.

4. The injector device according to claim 3, wherein throughout the range of movement of the first sleeve from the position in which the needle unit engages the cartridge to the second position, the second sleeve moves simultaneously with the first sleeve to expose the needle.

5. The injector device according to claim 1, wherein a spring is provided to resist movement of the second sleeve.

6. The injector device according to claim 1, further comprising:
   a plunger displaceable to drive medicament from the cartridge; and
   a plunger mechanism triggerable to displace the plunger during operation of the injector device.

7. The injector device according to claim 6, wherein either the first sleeve or the second sleeve are configured to trigger the plunger during displacement along the longitudinal axis.

8. The injector device according to claim 1, wherein the needle unit comprises a protrusion, and the resiliently displaceable arm comprises a corresponding opening through which the protrusion is locatable to connect the resiliently displaceable arm to the needle unit.

9. The injector device according to claim 8, wherein the protrusion is shaped so that, during use, with the needle unit located against the cartridge, further axial movement of the first sleeve causes the protrusion to displace the resiliently displaceable arm away from the longitudinal axis, and out of engagement with the needle unit.

10. The injector device according to claim 9, wherein the resiliently displaceable arm comprises an elongate slot distal to the corresponding opening to provide a track for the protrusion during the further axial movement of the resiliently displaceable arm.

11. The injector device according to claim 10, wherein an end of the resiliently displaceable arm is further provided with a clip, the clip being configured to lock over an edge of the cartridge when the first sleeve is in the second position.

12. The injector device according to claim 11, wherein the resiliently displaceable arm is provided with a delimitation to allow a portion of the resiliently displaceable arm comprising the elongate slot and the corresponding opening to move independently of the clip.

13. The injector device of claim 1, comprising a plurality of resiliently displaceable arms extending into the housing and into contact with the needle unit, wherein each resiliently displaceable arm is configured to disengage the needle unit by moving away from the longitudinal axis as the first sleeve is moved from the first position to the second position, thereby allowing the first sleeve to move independently of the needle unit.

14. An injector device comprising:
   a housing;
   a medicament cartridge received in the housing, wherein the medicament cartridge contains a medicament;
   a needle unit comprising a needle;
   a first sleeve slidable along a longitudinal axis of the housing from a first position, in which the first sleeve conceals the needle, to a second position, in which the needle is exposed from an end of the first sleeve,
      wherein the first sleeve is configured to engage the needle unit so that, during use, movement of the first sleeve from the first position to the second position moves the needle unit from a primary position to a secondary position, and
      wherein, in the secondary position, the needle unit is located over an end of the medicament cartridge when the medicament cartridge is received in the injector device; and
   a second sleeve arranged to move telescopically with respect to the first sleeve, the first sleeve configured to extend from the second sleeve when the first sleeve is in the first position, wherein the first sleeve comprises a resiliently displaceable arm extending into the housing and into contact with the needle unit, wherein the resiliently displaceable arm is configured to disengage from the needle unit by moving away from the longitudinal axis as the first sleeve is moved from the first position to the second position, thereby allowing the first sleeve to move independently of the needle unit.

15. A method of operating an injector device, the method comprising:
   moving a first sleeve of the injector device relative to a second sleeve of the injector device from a first position to a needle unit engagement position, wherein moving the first sleeve relative to the second sleeve comprises causing a needle unit of the injector device to move from a primary position in which the needle unit is disengaged from a cartridge of the injector device to a secondary position in which the needle unit is engaged to the cartridge; and
   moving the first sleeve with the second sleeve from the needle unit engagement position to a second position to expose a needle of the needle unit from an end of the first sleeve, wherein moving the first sleeve with the second sleeve comprises causing a resiliently displaceable arm of the first sleeve to move away from a longitudinal axis of a housing of the injector device to disengage from the needle unit,
   thereby allowing the first sleeve to move independently of the needle unit.

16. The method according to claim 15, wherein the end of the first sleeve is flush with an end of the second sleeve when the first sleeve is in the needle unit engagement position.

17. The method according to claim 15, wherein the needle of the needle unit is concealed while moving the first sleeve relative to the second sleeve from the first position to the needle unit engagement position.

18. The method according to claim 15, wherein moving the first sleeve with the second sleeve from the needle unit engagement position to the second position comprises initiating an injection of medicament from the injector device.

* * * * *